United States Patent [19]

Miyata et al.

[11] Patent Number: 4,547,620

[45] Date of Patent: Oct. 15, 1985

[54] PROCESS FOR REMOVING A HALOGEN COMPONENT DERIVED FROM A CATALYST FROM AN ORGANIC COMPOUND CONTAINING SAID HALOGEN COMPONENT

[75] Inventors: Shigeo Miyata; Noriko Iizima, both of Takamatsu, Japan

[73] Assignee: Kyowa Chemical Industry Co. Ltd., Tokyo, Japan

[21] Appl. No.: 583,308

[22] Filed: Feb. 24, 1984

[30] Foreign Application Priority Data

Feb. 28, 1983 [JP] Japan .................................. 58-30949

[51] Int. Cl.$^4$ ............................................... C07C 7/12
[52] U.S. Cl. .................... 585/852; 585/820; 585/868; 208/262
[58] Field of Search ............... 585/820, 852, 853, 868; 208/262

[56] References Cited

U.S. PATENT DOCUMENTS

| | | | |
|---|---|---|---|
| 2,413,871 | 1/1947 | Hepp | 585/852 |
| 3,222,415 | 12/1965 | Bloch | 585/852 |
| 4,117,023 | 9/1978 | Gillet et al. | 585/868 |

Primary Examiner—D. E. Gantz
Assistant Examiner—Chung K. Pak
Attorney, Agent, or Firm—Sherman & Shalloway

[57] ABSTRACT

A process for removing a halogen component from a halogen-containing organic compound, which comprises contacting an organic compound in the liquid state which is produced by using a halogen containing catalyst selected from the group consisting of Friedel-Crafts catalysts and Ziegler catalysts and contains the halogen component derived from said catalyst, with a hydrotalcite compound represented by the formula

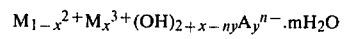

$$M_{1-x}^{2+}M_x^{3+}(OH)_{2+x-ny}A_y^{n-}\cdot mH_2O$$

wherein $M^{2+}$ represents a divalent metal ion selected from the group consisting of $Mg^{2+}$, $Zn^{2+}$, $Ca^{2+}$, $Ni^{2+}$, $Co^{2+}$, $Mn^{2+}$ and $Cu^{2+}$, $M^{3+}$ represents a trivalent metal ion selected from the group consisting of $Al^{3+}$, $Fe^{3+}$ and $Cr^{3+}$, $A^{n-}$ represents an anion having a valence of n selected from the group consisting of $HCO_3^-$, $OH^-$ and $CO_3^{2-}$, and x, y and m are each a positive number and satisfy the following conditions $0.1 < x < 0.5$, $0.1 < y < 0.4$, $0 \leq m < 1$, under non-aqueous conditions, and separating the treated organic compound from the hydrotalcite compound.

14 Claims, No Drawings

PROCESS FOR REMOVING A HALOGEN COMPONENT DERIVED FROM A CATALYST FROM AN ORGANIC COMPOUND CONTAINING SAID HALOGEN COMPONENT

This invention relates to a process for removing a halogen component from an organic compound which is produced by using a halogen-containing catalyst such as a Friedel-Crafts catalyst or Ziegler catalyst and contains the halogen component derived from the catalyst. Specifically, it relates to a process for removing the aforesaid halogen component by an anion exchange reaction under non-aqueous conditions.

According to this process, the halogen component (anion) can be removed from the organic compound by a very advantageous and simpler treating operation than disadvantageous and complex treating operation in the prior art and with an improved high removing effect. The process of this invention brings about other advantages. For example, catalytic metal components (cation) can also be captured and removed. Since the removing treatment can be carried out at relatively high temperatures, the treating time can be shortened. There is no likelihood of adverse effects, such as coloration, the generation of hydrogen halides and the reduction of electrical insulation, on the organic compound treated. The treating agent can be easily separated from the treated organic compound, and can be regenerated easily.

More specifically, this invention pertains to a process for removing a halogen component from a halogen-containing organic compound, which comprises contacting an organic compound in the liquid state which is produced by using a halogen-containing catalyst selected from the group consisting of Friedel-Crafts catalyst and Ziegler catalysts and contains the halogen component derived from said catalyst, with a hydrotalcite compound represented by the following formula

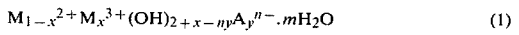

$$M_{1-x}^{2+}M_x^{3+}(OH)_{2+x-ny}A_y^{n-}\cdot mH_2O \qquad (1)$$

wherein $M^{2+}$ represents a divalent metal ion selected from the group consisting of $Mg^{2+}$, $Zn^{2+}$, $Ca^{2+}$, $Ni^{2+}$, $Co^{2+}$, $Mn^{2+}$ and $Cu^{2+}$, $M^{3+}$ represents a trivalent metal ion selected from the group consisting of $Al^{3+}$, $Fe^{3+}$ and $Cr^{3+}$, $A^{n-}$ represents an anion having a valence of n selected from the group consisting of $HCO_3^-$, $OH^-$ amd $CO_3^{2-}$, and x, y and m are each a positive number and satisfy the following conditions $0.1 < x < 0.5$, $0.1 < y < 0.4$, $0 \leq m < 1$, under non-aqueous conditions, and separating the treated organic compound from the hydrotalcite compound.

Halogen-containing catalysts, for example a Friedel-Crafts catalyst such as $AlCl_3$, $FeCl_3$, $SnCl_4$, $BF_3$ and other Lewis acids, or a Ziegler catalyst composed of a transition metal catalyst component, for example a transition metal halogen compound such as a halogen-containing vanadium or titanium compound, or a transition metal-containing compound derived from such a halogen-containing transition metal compound, a magnesium or manganese compound and an electron donor compound, and an organometallic compound catalyst component such as an organoaluminum compound have been extensively used in alkylation reactions and the polymerization or copolymerization reactions of olefins.

For example, such halogen-containing catalysts are used for the production of various compounds having a high to a low molecular weight, such as ethylbenzene, polyacetal, oligomers of olefins (lubricant oils), anion exchange resins, petroleum resins, polyisobutene, butyl rubber, polybutadiene, polyisoprene, polyethylene, polypropylene, polymethylpentene and olefin copolymers.

The insufficient removal of the catalysts, particularly their halogen component, from such organic compounds causes various troubles such as the coloration of the resulting organic compounds, the generation of hydrogen halides by the thermal decomposition of the catalysts, the degradation or decomposition of the organic compounds and the deterioration of the properties of the organic compounds. It is necessary therefore to remove the halogen component fully from these organic compounds. The removing operation, however, requires complex and disadvantageous treatments, and even by such a complex and disadvantageous operation, the halogen component cannot be fully removed.

In the prior art, washing with water and/or an aqueous alkaline solution has been most commonly employed for the removal of the halogen-containing catalyst components from such organic compounds. Washing with water, for example, has the difficulty that after the treatment, the organic compound layer can be separated from the washing water layer only with a poor efficiency, and consequently, the yield of the organic compounds recovered is reduced. Furthermore, enormous amounts of labor and complex and large facilities are required for treating the separated water layer. Even when the water-washing treatment is carried out in spite of such disadvantages, no satisfactory removing effect can be achieved. The treatment with an aqueous alkaline solution cannot essentially be free from the poor efficiency of separation between the oil layer and the aqueous layer. In addition, since the alkali leads to the formation of a colloidal hydroxide precipitate, an additional labor and operation and an additional facility are required for removing the by-product precipitate which is very difficult to separate by filtration. A fully satisfactory removing efficiency cannot be achieved, either, by the treatment with the aqueous alkaline solution.

The present inventors have made extensive investigations in order to develop a process of removing a halogen component from an organic compound which is produced by using such a halogen-containing catalyst as described above and contains the halogen component derived from the catalyst, while industrially advantageously overcoming the many troubles which are encountered in the removal of the halogen component by the prior art.

These investigations have led to the discovery that the hydrotalcite compounds of general formula (1) given above have the property of capturing the halogen component of the aforesaid organic compounds in the liquid state by anion exchange reaction under non-aqueous conditions (under conditions free from a substantial amount of water), and that the aforesaid troubles can thus be overcome advantageously, and within short periods of time, the halogen component can be industrially advantageously removed from the organic compounds containing the halogen-containing catalysts.

It has not been known that the hydrotalcite compounds of formula (1) show the property of capturing the halogen component (anion) of the organic compounds in the liquid state under non-aqueous conditions by anion exchange reaction. It has been found that the aforesaid hydrotalcite compounds of formula (1) also have the property of occluding catalytic metal components (cations) such as $Al^{3+}$, $Ti^{3+}$ and $Ti^{4+}$ in their crystal surfaces or reactively capturing them, and moreover, simultaneously with the capturing of the halogen component by anion exchange reaction, show the ability to neutralize the acid to bring the pH of the system nearly to neutrality.

Furthermore, since the hydrotalcite compounds of formula (1) stably fix the halogen component captured under non-aqueous conditions, and do not liberate it at a temperature of up to about 400° C., the halogen removing treatment can be carried out at relatively high temperatures and the halogen component can be captured within a short period of time. Another advantage is that since the compounds of formula (1) are substantially insoluble both in water and in oils, the inclusion of a small amount of it in the organic compound treated is not likely to cause such troubles as coloration and the generation of hydrogen halide, and no inconvenience such as the reduction of electrical insulation occures. It has also been found that since the hydrotalcite compounds of formula (1) have good sedimentability and filtrability, they can be separated from the organic compound treated by a very easy operation, and moreover, they can be regenerated and reused.

Japanese Patent Publication No. 3353/1977 (Laid-Open Patent Publication No. 69780/1973 laid-open on Sept. 21, 1973) discloses that compounds which overlap the hydrotalcite compounds of formula (1) above can be used for exchange or adsorption of ions as crystalline inorganic ion exchangers. This patent document, however, quite fails to disclose or suggest that the compounds of formula (1) have the ability to capture the halogen component of a halogen-containing organic compound in the liquid state by anion exchange reaction under non-aqueous conditions. It neither discloses nor suggests that under non-aqueous conditions, these hydrotalcite compounds can capture and remove the halogen component from a halogen-containing organic compound in the liquid state with the aforesaid excellent advantages and a high removing effect.

It is usual and well known that an ion exchange reaction takes place in an aqueous medium. It has now been found in accordance with the present invention that the hydrotalcite compounds of formula (1) can advantageously capture the halogen component of a halogen-containing organic compound in the liquid state, which is prepared in the presence of a halogen-containing catalyst, under non-aqueous conditions, and the many troubles associated with the catalyst removal treatments in accordance with the prior art can all be removed by the process of this invention.

It is an object of this invention to provide a process for removing a halogen component from an organic compound containing a halogen-containing catalyst with industrial advantages.

The above and other objects and advantages of this invention will become more apparent from the following description.

The hydrotalcites of formula (1) used in the process of this invention can be produced, for example, in accordance with the process disclosed in Japanese Patent Publication No. 3353/1977. For example, they can be produced by reacting (a) a compound of a divalent cation $M^{2+}$ selected from $Mg^{2+}$, $Zn^{2+}$, $Ca^{2+}$, $Ni^{2+}$, $Co^{2+}$, $Mn^{2+}$ and $Cu^{2+}$, (b) a compound of a trivalent cation $M^{3+}$ selected from $Al^{3+}$, $Fe^{3+}$ and $Cr^{3+}$, (c) a compound of an anion $A^{n-}$ ($n=1-2$) selected from $HCO_3^-$, $CO_3^{2-}$ and $OH^-$, and (d) a substance capable of yielding $OH^-$, in a liquid medium, preferably in an aqueous medium, so that the relations $0.1<x<0.5$ and $0.1<y<0.4$ are satisfied.

Preferably, the reaction may be carried out with sufficient stirring at a temperature of, for example, not more than about 350° C. and a pH of at least about 6. The reaction can also be carried out under elevated pressure. For example, the reaction can be carried out at room temperature to about 350° C. and atmospheric pressure to about 300 atmospheres. When the reaction materials are difficultly soluble or insoluble in the liquid medium, it is advisable to heat them at a temperature of, for example, about 60° to about 350° C. for about 3 to about 5 hours. The reaction time is, for example, about 0.5 to about 5 hours. After the reaction, the resulting difficultly soluble or insoluble precipitate is collected, and, for example, washed with water and dried at a temperature of, for example not more than about 150° C. to give the hydrotalcite compound of formula (1).

Examples of the compound of $M^{2+}$ (a) and the compound of $M^{3+}$ (b) used in the above reaction include the halides, nitrates, sulfates, organic acid salts, alcohol salts, alkali metal aluminum salts, hydroxides, basic carbonates, carbonates, basic organic acid salts, and oxides of the metals selected from the group of $M^{2+}$ and $M^{3+}$.

The compound of the anion $A^{n-}$ (c) used in the above reaction may be a compound capable of yielding $HCO_3^-$, $CO_3^{2-}$ and $OH^{31}$ in the liquid medium. Specific examples include sodium hydrogen carbonate, potassium hydrogen carbonate, sodium carbonate, potassium carbonate, ammonium carbonate, sodium hydroxide, potassium hydroxide, ammonia, urea and calcium hydroxide.

Examples of the substance capable of yielding $OH^-$ (d) used in the above reaction include alkali metals, alkaline earth metals, the oxides, hydroxides and carbonates of these metals, ammonium hydroxide, and ammonia gas.

The reaction can be carried out batchwise or continuously, or by any other desired modes. Industrially, the continuous process is advantageous in view of its good reproducibility and the excellent stability of the crystallinity of the resulting product.

In performing the continuous process, aqueous solutions or suspensions of the compounds (a), (b), (c) and (d) may be used separately, or a mixed aqueous solution or suspension of the compounds (a) and (b) may be used in combination with solutions of the compounds (c) and (d) or a mixed solution of the compounds (c) and (d). In performing the batchwise process, the operating sequence may be varied. For example, the compounds (c) and (d) may be added to an aqueous solution or suspension containing $(1-x)$ moles of the compound (a) and x moles of the compound (b) and reacted. Or it is possible to react $(1-x)$ moles of the compound (a) with the compound (d) to form $M^{2+}(OH)_2$, and therefore react it with x moles of the compound (b), y moles of the compound (c) and the compound (d). When the counter ion of the compound (a) or (b) corresponds to $A^{n-}$, it is sometimes unnecessary to supply the compound (c).

To promote crystallization of the product, the reaction is carried out preferably at relatively high temperatures and pressures. This purpose can also be achieved by hydrothermally treating a slurry of the product in an aqueous medium at a relatively high temperature of about 150° to about 350° C. and a relatively high pressure of, for example, about 5 to about 300 atmospheres, preferably with sufficient stirring, for a period of, for example, about 5 to about 15 hours.

According to the process of this invention, the hydrotalcite compound of the following formula (1) which can be obtained as above or is commercially available,

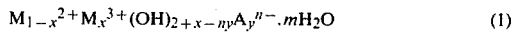

$$M_{1-x}^{2+}M_{x}^{3+}(OH)_{2+x-ny}A_y^{n-}\cdot mH_2O \qquad (1)$$

wherein $M^{2+}$ represents a divalent metal ion selected from the group consisting of $Mg^{2+}$, $Zn^{2+}$, $Ca^{2+}$, $Ni^{2+}$, $Co^{2+}$, $Mn^{2+}$ and $Cu^{2+}$, $M^{3+}$ represents a trivalent metal ion selected from the group consisting of $Al^{3+}$, $Fe^{3+}$ and $Cr^{3+}$, $A^{n-}$ represents an anion having a valence of n selected from the group consisting of $HCO_3^-$, $OH^-$ and $CO_3^{2-}$, and x, y and m are each a positive number and satisfy the following conditions $0.1 < x < 0.5$ (preferably $0.2 \leq x < 0.5$), $0.1 < y < 0.4$ (preferably $0.2 \leq y < 0.4$), $0 \leq m < 1$, is contacted under non-aqueous conditions with an organic compound in the liquid state which is obtained by using a halogen-containing catalyst selected from the group consisting of Friedel-Crafts catalysts and Ziegler catalysts and contains the halogen component derived from the catalyst, and thereafter, the hydrotalcite compound is separated from the treated organic compound. As a result, the halogen component in the organic compound can be easily removed to an order of below several ppm.

In the above formula (1), a divalent metal ion selected from $Mg^{2+}$, $Zn^{2+}$, $Ca^{2+}$ and $Ni^{2+}$ is preferred as $M^{2+}$, and a divalent metal ion selected from $Mg^{2+}$ and $Zn^{2+}$ is more preferred. $M^{3+}$ is preferably a trivalent metallic ion selected from $Al^{3+}$ and $Fe^{3+}$, and more preferably $Al^{3+}$. $A^{n-}$ is preferably an anion having a valence of n selected from $OH^-$ and $CO_3^{2-}$.

The compound of formula (1) has a BET specific surface area of preferably about 5 to about 150 m²/g, more preferably about 20 to about 150 m²/g.

Under non-aqueous conditions, the hydrotalcite compound of formula (1) shows the property of capturing the halogen compound of a halogen-containing organic compound in which the halogen component is derived from a halogen-containing catalyst by anion exchange reaction, and further has the property of occluding the metallic components of the catalyst such as $Al^{3+}$, $Ti^{3+}$ and $Ti^{4+}$ in the crystal surface of the hydrotalcite compound of formula (1) or reactively capturing such metallic components. Furthermore, the hydrotalcite compound of formula (1) has the ability to neutralize the acid simultaneously with the capturing of the halogen compound by anion exchange reaction, and thus adjust the pH of the system nearly to neutrality. The halogen component which has been taken up into the hydrotalcite compound of formula (1) by anion exchange reaction is stable, and is not liberated at a temperature of up to about 400° C. Furthermore, because the hydrotalcite compound of formula (1) is substantially insoluble in water and oils and has the aforesaid heat stability, the remaining of a small amount of it in the treated organic compound is not likely to cause such troubles as the coloration of the organic compound or the generation of hydrogen halide or inconveniences such as the reduced electrical insulation of the organic compound.

The reaction of the hydrotalcite compound of formula (1) to capture and remove the halogen component proceeds more rapidly as the temperature of the treating system becomes higher. Accordingly, it is preferred to contact the hydrotalcite compound of formula (1) at relatively high temperatures under non-aqueous conditions with the organic compound in the liquid state containing a halogen component derived from a halogen-containing catalyst. The heat stability of the hydrotalcite compound of formula (1) also has the advantage of enabling the treatment to be performed under these conditions. Furthermore, since the ability of the hydrotalcite compound of formula (1) to capture the halogen component greatly tends to depend upon the amount (x) of the $M^{3+}$ metal, it is preferred to select a compound of formula (1) which has a large x value.

In the practice of the process of this invention, the mode of contacting the hydrotalcite compound of formula (1) with the halogen-containing organic compound may be chosen freely. The non-aqueous conditions mean a system which does not contain a substantial amount of water, and are not intended to exclude a small amount of water which may be present in an organic compound which is itself in the liquid state or a solution of the organic compound in a non-aqueous solvent.

For example, when the organic compound containing a halogen-containing catalyst which is produced by using the aforesaid catalyst with or without subsequent isolation is liquid (non-aqueous liquid organic compound), the organic compound is contacted with the hydrotalcite compound of formula (1) and then the two are separated from each other using any desired solid-liquid separating means. As a result, the halogen component in the organic compound can be removed to an order of, for example, several ppm by a very simple treating operation. When the organic compound produced by using the aforesaid catalyst is in the form of a solution in a non-aqueous solvent, (if the organic compound produced is a solid, it is first dissolved in a suitable non-aqueous solvent), the solution of the organic compound in the non-aqueous solvent is contacted with the hydrotalcite compound of formula (1), and by the same procedure as in the above embodiment, the halogen component can be captured and removed. Since the hydrotalcite compound of formula (1) has good sedimentability and filtrability, the separating operation after the contacting treatment is easy, and the halogen component can be removed very advantageously industrially over conventional catalyst removing operations.

In the performance of the process of this invention, the hydrotalcite compound of formula (1) can be used in any desired form such as a powder, granules, or particles. In the form of a powder, too, the hydrotalcite compound has good sedimentability and filtrability. To improve these properties, the hydrotalcite compound of formula (1) may be used after it has been granulated and molded into a suitable shape. Thus, an embodiment may be employed in which the hydrotalcite compound in this shape is filled in a column, and the organic compound to be treated is passed through the column, thereby contacting both. Furthermore, in separating the hydrotalcite compound from the treated organic compound, it is a also possible to add a suitable amount of water to the treated organic compound to move the hydrotalcite compound to the aqueous layer which is then removed.

As stated above, the hydrotalcite compound of formula (1) has the property of capturing by anion exchange reaction the halogen component (anion) such as chlorine, bromine or fluorine of an organic compound which is produced by using a halogen-containing catalyst and in which the halogen component is derived from the catalyst, and also of capturing almost all metals other than alkali metals in the organic compound, for example the metallic components (cations) of the catalyst such as $Al^{3+}$, $Ti^{3+}$, and $Ti^{4+}$. Accordingly, when it is utilized for removing the halogen component of an organic compound produced by using $AlCl_3$ as a Fridel-Crafts catalyst, it shows the unique property of capturing not only the chlorine ion, but also simultaneously a considerable amount of the aluminum ion.

In the practice of the process of this invention, the used hydrotalcite compound of formula (1) can be re-used after regeneration. The regeneration can be easily carried out by washing the hydrotalcite compound of formula (1) with an aqueous solution of a water-soluble compound capable of yielding $A^{n-}$, such as sodium hydroxide, sodium hydrogen carbonate and sodium carbonate, to subject the halogen component captured by the contacting treatment to ion exchange with $A^{n-}$. The washing temperature may, for example, be room temperature to about 100° C. Accordingly, when the process of this invention is to be carried out by using the column method described above, the halogen component of the organic compound in the liquid state in which the halogen component is derived from a halogen-containing catalyst can be removed industrially advantageously by alternately performing the operation of capturing and removing the halogen component and the operation of washing and regenerating the hydrotalcite compound.

Since the hydrotalcite compound of formula (1) has excellent heat stability as stated hereinabove, its contacting with the aforesaid halogen-containing organic compound can be carried out at a temperature of up to about 350° C., preferably up to about 300° C. Use of high temperatures has the advantage of promoting the capturing of the halogen component. This is advantageous and less costly over and than the use of an anion exchange resin, for example.

The process of this invention can be broadly used to remove the halogen component of an organic compound which is produced by using a halogen-containing catalyst selected from the group consisting of Friedel-Crafts catalysts and Ziegler catalysts.

Such Friedel-Crafts catalysts are well known, and may, for example, include at least one of halides of metals of Groups II to VI or VIII of the periodic table, such as $ZnCl_2$, $AlCl_3$, $BF_3$, $SnCl_4$, $TiCl_4$, $BiCl_3$, $SbCl_5$, $TeCl_2$, $TeCl_4$ and $FeCl_3$, and a combination of it with an inorganic acid such as HCl, HF, $H_2SO_4$, $P_2O_5$ and $H_3PO_4$. The Ziegler catalysts are also well known, and include, for example, combinations of a halogen-containing transition metal compound, for example a halogen-containing vanadium or titanium compound such as vanadium oxyhalides, vanadium halides, titanium halides and titanium alkoxides, or a halogen-containing transition metal compound component derived from the aforesaid component and an electron donor and/or a magnesium or manganese compound, with an organometallic compound component of a metal of Groups I to III of the periodic table, and combinations of these combination catalysts with electron donors.

Examples of organic compounds containing such halogen-containing catalysts include ethylbenzene, polyacetal, oligomers of olefins (lubricant oils), anion exchange resins, petroleum resins, polyisobutene, butyl rubber, polybutadiene, polyisoprene, polymers of $C_{2-8}$ olefins (such as polyethylene, polypropylene and polymethylpentene), copolymers of at least two of $C_{2-8}$ olefins, and copolymers of at least one $C_{2-8}$ olefin and a diolefin.

The following examples illustrate the process of this invention more specifically.

EXAMPLE 1

Benzene and ethylene were reacted in the presence of a Friedel-Crafts catalyst system (composed of $AlCl_3$ and HCl). The resulting ethylbenzene was washed with water to give ethylbenzene containing 2100 ppm, calculated as Cl, of a residue of the catalyst.

One kilogram of the ethylbenzene was passed through a column having a diameter of 4 cm and filled with 200 g of pellets with a diameter of 1.5 cm of hydrotalcite $Mg_{0.7}Al_{0.3}(OH)_{2.3}.0.5H_2O$. The resulting ethylbenzene contained 8 ppm, calculated as Cl, of the catalyst.

COMPARATIVE EXAMPLE 1

Five hundred grams of a 1 mole/liter aqueous solution of sodium hydroxide was added to the ethylbenzene containing 2100 ppm of Cl used in Example 1, and the mixture was fully stirred. The aqueous layer was then separated. Then, 500 g of water was added to the ethylbenzene, and the mixture was fully stirred, followed by separating the aqueous layer. Subsequently, 500g of water was added twice and the same treatment was carried out. The resulting ethylbenzene contained 120 ppm of chlorine.

EXAMPLE 2

A 1-liter glass autoclave was charged with 15 g of aluminum chloride, and with stirring, 600 g of octene-1 was gradually added dropwise and polymerized at 60° C. for 3 hours to obtain octene-1 oligomer for use as a lubricant oil.

Then, 90 g of hydrotalcite $Mg_{0.67}Al_{0.33}(OH)_{2.33}.0.52H_2O$) (BET specific surface area 120 $m^2/g$) was added to the resulting polymerization reaction product, and the mixture was stirred at 70° C. for 30 minutes. Then, the oligomer was separated from the hydrotalcite by filtration, and the chlorine content and aluminum content of the treated oligomer were measured. It was found to contain 16 ppm of chlorine and 0.2 ppm of aluminum.

COMPARATIVE EXAMPLE 2

Example 2 was repeated except that 80 ml of an aqueous solution containing 25 g of sodium hydroxide was added instead of the hydrotalcite, and the oligomer was treated at 70° C. for 1 hour. As a result, the treated oligomer was found to contain 157 ppm of chlorine and 12 ppm of aluminum.

EXAMPLE 3

Two grams of hydrotalcite $Zn_{0.75}Al_{0.25}$--$(CO_3)_{0.125}.0.52H_2O$ (spray-granulated to a diameter of about 200 to 300 microns and having a BET specific surface area of 85 m²/g) was added to 400 g of the octene-1 oligomer containing 157 ppm of chlorine which was obtained in Comparative Example 2. The mixture was stirred at 90° C. for about 30 minutes. The mixture was then filtered to give purified octene-1 oligomer containing 2 ppm of chlorine and 0.8 ppm of aluminum.

EXAMPLE 4

Polyisoprene obtained by continuously polymerizing isoprene in hexane in the presence of a Ziegler catalyst (composed of $TiCl_4$ and $Al(n-C_4H_9)_3$) was washed to obtain polyisoprene containing 1500 ppm, calculated as chlorine, of the catalyst residue. Four hundred grams of the polyisoprene was dissolved in 5 liters of hexane, and 10 g of hydrotalcite $Mg_{0.75}Al_{0.25}-(OH)_2(CO_3)_{0.125}.0.5-H_2O)$ powder was added. The mixture was stirred at about 50° C. for 30 minutes. Then, the mixture was filtered to separate the hydrotalcite, and the polyisoprene was dried. The final dried polyisoprene contained 15 ppm, calculated as chlorine, of the catalyst residue.

EXAMPLE 5

Ethylene, propylene and dicyclopentadiene were solution-polymerized at a temperature of 56° C. and a pressure of 2 atmospheres in the presence of a catalyst composed of a 0.5 mmol/l hexane solution of $VOCl_3$ and a 2.5 mmole/l hexane solution of $(C_2H_5)_{1.5}AlCl_{1.5}$. The volume ratio of propylene to ethylene was maintained at 3:2.

To 2 kg of a hexane solution of 40 g of the resulting ethylene/propylene/diene copolymer rubber (containing 110 ppm of Cl) was added 4 g of hydrotalcite $Mg_{0.7}Al_{0.3}(OH)_2(CO_3)_{0.15}.0.48H_2O$ (having a BET specific surface area of 32 m²/g and spray-granulated to a diameter of about 500 microns). The mixture was stirred at 80° C. for 30 minutes. The polymer was then separated from the hydrotalcite by filtration to obtain a hexane solution of the ethylene/propylene/diene copolymer rubber from which the catalyst residue was removed. The hexane solution was then dried, and the dried ethylene/propylene/diene rubber was taken out. The rubber was found to contain 32 ppm of chlorine.

EXAMPLE 6

Using an isopentane solution of $AlBr_3$ (Friedel-Crafts catalyst), isoprene and isobutylene were solution-polymerized in isopentane as a solvent at $-101°$ to $-99°$ C.

Two kilograms of an isopentane solution of the resulting butyl rubber (butyl rubber concentration 4.5%; Br concentration 4.94%) was charged at about 20° C. onto the top of a column having a diameter of 5 cm and filled with 500 g of hydrotalcite $Zn_{0.6}Al_{0.4}(OH)_2-(H-CO_3^-)_{0.4}.0.12H_2O$ granulated to spherical granules having a diameter of 1 mm and having a BET specific surface area of 87 cm²/g, and an isopentane solution containing the butyl rubber dissolved therein was recovered from the bottom of the column. The recovered butyl tubber solution was dried to give purified butyl rubber which was found to contain 0.1 ppm of Al and 18 ppm of Br as the catalyst residue.

EXAMPLE 7

Benzene was alkylated with propylene using $AlCl_3$ as a Friedel-Crafts catalyst to synthesize cumene and then most of the catalyst was separated by a gravity-type sedimentation technique. To one liter of the resulting liquor containing 70% by weight of cumene and other alkylbenzenes, 30% by weight of benzene, and 520 mg/liter of $AlCl_3$ (Al=105 ppm, Cl=415 ppm) was added 4 g of a powder of hydrotalcite $Ni_{0.7}Al_{0.3}(OH)_2-(CO_3)_{0.15}.0.52H_2O$ having a BET specific surface area of 112 m²/g. The mixture was stirred at 50° C. for 30 minutes, and then filtered to separate the hydrotalcite, and obtain a solution containing purified cumene. The solution was found to contain 0.1 ppm of Al and 7.5 ppm of Cl.

What we claim is:

1. A process for removing a halogen component from a halogen-containing organic compound, which comprises contacting an organic compound in the liquid state which is produced by using a halogen containing catalyst selected from the group consisting of Freidel-Crafts catalysts and Ziegler catalysts and contains the halogen conponent derived from said catalyst, with a hydrotalcite compound represented by the formula

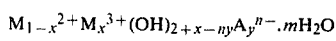

$$M_{1-x}^{2+}M_x^{3+}(OH)_{2+x-ny}A_y^{n-}.mH_2O$$

wherein $M^{2+}$ represents a divalent metal ion selected from the group consisting of $Mg^{2+}$, $Zn^{2+}$, $Ca^{2+}$, $Ni^{2+}$ + $Co^{2+}$, $Mn^{2+}$, and $Cu^{2+}$, $M^{3+}$ represents a trivalent metal ion selected from the group consisting of $Al^{3+}$, $Fe^{3+}$ and $Cr^{3+}$, $A^{n-}$ represents an anion having a valence of n selected from the group consisting of $HCO_3^-$, $OH^-$ and $CO_3^{2-}$, and x,y and m are each a positive number and satisfy the following conditions $0.1 < x < 0.5$, $0.1 < y < 0.4$, $1 \leq m < 1$, under non-aqueous conditions and at a temperature at which the halogen component which has been taken up by the hydrotalcite compound is not liberated, and separating the treated organic compound from the hydrotalcite compound.

2. The process of claim 1 wherein x, y and m satisfy the following conditions $0.2 \leq x < 0.5$, $0.2 \leq y < 0.4$, $0 \leq m < 1$.

3. The process of claim 1 wherein the contacting is carried out at a temperature of up to about 350° C.

4. The process of claim 1 wherein the hydrotalcite compound has a BET specific surface area of about 5 to about 150 m²/g.

5. The process of claim 1 wherein the contacting is at a temperature below about 400° C.

6. The process of claim 1 wherein $M^{2+}$ is selected from the group consisting of $Mg^{2+}$, $Zn^{2+}$, $Ca^{2+}$, and $Ni^{2+}$.

7. The process of claim 6 wherein $M^{3+}$ is $Al^{3+}$ or $Fe^{3+}$.

8. The process of claim 1 wherein $M^{2+}$ is $Mg^{2+}$ or $Zn^{2+}$.

9. The process of claim 8 wherein $M^{3+}$ is $Al^{3+}$.

10. The process of claim 1 wherein $M^{3+}$ is $Al^{3+}$ or $Fe^{3+}$.

11. The process of claim 1 wherein $M^{3+}$ is $Al^{3+}$.

12. The process of claim 1 wherein $A^{n-}$ is $OH^-$ or $CO_3^{2-}$.

13. The process of claim 12 wherein $M^{2+}$ is $Mg^{2+}$, $Zn^{2+}$, $Ca^{2+}$, or $Ni^{2+}$ and $M^{3+}$ is $Al^{3+}$ of $Fe^{3+}$.

14. The process of claim 1 wherein the hydrotalcite compound has a BET specific surface area of from about 20 to about 150 m²/g.

* * * * *

UNITED STATES PATENT AND TRADEMARK OFFICE
CERTIFICATE OF CORRECTION

PATENT NO. : 4,547,620
DATED : October 15, 1985
INVENTOR(S) : SHIGEO MIYATA, ET AL.

It is certified that error appears in the above-identified patent and that said Letters Patent is hereby corrected as shown below:

IN THE CLAIMS

Claim 1, line 12, (Column 10, line 25), insert --,-- between "$Ni^{2+}$" and "$Co^{2+}$".

Signed and Sealed this

Twenty-fourth Day of December 1985

[SEAL]

Attest:

DONALD J. QUIGG

Attesting Officer     Commissioner of Patents and Trademarks